(12) United States Patent
Kono

(10) Patent No.: US 7,354,910 B2
(45) Date of Patent: Apr. 8, 2008

(54) AGENT FOR TREATING INFLAMMATORY BOWEL DISEASES

(75) Inventor: Toru Kono, Asahikawa (JP)

(73) Assignee: Seikagaku Kogyo Kabushiki Kaisha, Tokyo (JP)

(*) Notice: Subject to any disclaimer, the term of this patent is extended or adjusted under 35 U.S.C. 154(b) by 527 days.

(21) Appl. No.: 10/492,947

(22) PCT Filed: Oct. 17, 2002

(86) PCT No.: PCT/JP02/10799

§ 371 (c)(1),
(2), (4) Date: Oct. 20, 2004

(87) PCT Pub. No.: WO03/033004

PCT Pub. Date: Apr. 24, 2003

(65) Prior Publication Data

US 2005/0043270 A1    Feb. 24, 2005

(30) Foreign Application Priority Data

Oct. 18, 2001  (JP) .............................. 2001-320658

(51) Int. Cl.
*A61K 31/728* (2006.01)

(52) U.S. Cl. ...................................... 514/54
(58) Field of Classification Search ........... 514/54
See application file for complete search history.

(56) References Cited

U.S. PATENT DOCUMENTS

| 4,141,973 A |   | 2/1979 | Balazs |
|---|---|---|---|
| 4,725,585 A | * | 2/1988 | Wenge et al. ............... 514/54 |
| 5,234,914 A |   | 8/1993 | Gallina |
| 5,811,410 A | * | 9/1998 | Falk et al. ................... 514/54 |

FOREIGN PATENT DOCUMENTS

| WO | WO 00/29030 A1 | 5/2000 |
|---|---|---|
| WO | WO 01/58457 A1 | 8/2001 |

OTHER PUBLICATIONS

Verspaget, H. et al "Diminished neutrophil function in Crohn's disease and ulcerative colitis . . . " Gut (1988) vol. 29, pp. 223-228.*
Zhang, K. et al "Influence of polysaccharides on neutrophil function . . . " J. Cell. Biochem. (1994) vol. 56, pp. 225-235.*
International Search Report dated Nov. 26, 2002.
XP-002400776,(1978) "The glycosaminoglycans of the human colon in inflammatory and neoplastic conditions", vol. 102, No. 3, abstract only.
XP-002400778 (1999) "Kallikrein-kinin system inhibitor—contains acid muco-polysaccharide", Derwent Publications Ltd.
Supplementary Partial European Search Report dated Oct. 10, 2006.

* cited by examiner

*Primary Examiner*—Leigh C. Maier
(74) *Attorney, Agent, or Firm*—Sughrue Mion, PLLC

(57) ABSTRACT

An agent for treating inflammatory bowel diseases and an agent for preventing or improving symptoms accompanied by inflammatory bowel diseases, which each comprises hyaluronic acid or a pharmaceutically acceptable salt thereof as an active ingredient.

17 Claims, 3 Drawing Sheets
(2 of 3 Drawing Sheet(s) Filed in Color)

AGENT FOR TREATING INFLAMMATORY BOWEL DISEASES

TECHNICAL FIELD

The present invention relates to an agent for treating inflammatory bowel diseases, which comprises hyaluronic acid or a pharmaceutically acceptable salt thereof as an active ingredient. Also, the present invention relates to an agent for preventing or improving symptoms accompanied by inflammatory bowel diseases (diarrhea, weight loss, bowel tissue edema, cell infiltration, surviving period shortening, and the like), which comprises hyaluronic acid or a pharmaceutically acceptable salt thereof as an active ingredient.

BACKGROUND ART

JP-A-11-147901 discloses a kallikrein-kinin system inhibitor which comprises, as an active ingredient, at least one selected from the group consisting of acidic mucopolysaccharides and physiologically acceptable salts thereof, and hyaluronic acid is disclosed as an example of the acidic mucopolysaccharides. In addition, the same document discloses an agent for treating or preventing acute colitis and chronic colitis, which comprises poly-sulfated hyaluronic acid as an active ingredient.

However, the above document does not disclose a test in which hyaluronic acid or poly-sulfated hyaluronic acid was actually administered to an animal of inflammatory bowel diseases, but discloses only an enzymological in vitro test on the inhibitory action of a kallikrein-kinin system. From the viewpoint of technical common sense in the technical field, it cannot be judged based on only such an in vitro test that it is effective for an animal of inflammatory bowel diseases. What is more, since the kallikrein-kinin system is not always considered to be the factor relating to the inflammatory bowel diseases, and other various factors are intricately entangled therein, it cannot be judged directly from the inhibitory activity of a kallikrein-kinin system that hyaluronic acid and poly-sulfated hyaluronic acid have markedly excellent effect on the inflammatory bowel diseases.

Although "an agent for treating or preventing acute colitis and chronic colitis, which comprises poly-sulfated hyaluronic acid as an active ingredient" is disclosed in the same document, the poly-sulfated hyaluronic acid is a substance which is physically and pharmacologically completely different from hyaluronic acid in terms that it has a sulfate group. Accordingly, even when the "poly-sulfated hyaluronic acid" is replaced with "hyaluronic acid", the agent comprising hyaluronic acid does not always have the same activity as that comprising poly-sulfated hyaluronic acid.

In addition, the above document neither discloses nor suggests the agent for preventing or improving various specific symptoms accompanied by inflammatory bowel diseases (diarrhea, weight loss, bowel tissues edema, cell infiltration, surviving period shortening, and the like), which comprises hyaluronic acid as an active ingredient.

DISCLOSURE OF THE INVENTION

An object of the present invention is to provide an agent for treating inflammatory bowel diseases, which comprises hyaluronic acid or a pharmaceutically acceptable salt thereof as an active ingredient, has high safety and is clinically and markedly effective.

Another object of the present invention is to provide an agent for preventing or improving symptoms accompanied by inflammatory bowel diseases (diarrhea, weight loss, bowel tissue edema, cell infiltration, surviving period shortening, and the like), which has high safety and is clinically and markedly effective.

The present invention provides an agent for treating inflammatory bowel diseases, which comprises hyaluronic acid or a pharmaceutically acceptable salt thereof as an active ingredient (hereinafter referred to as "treating agent of the invention").

Furthermore, the present invention provides an agent for preventing or improving symptoms accompanied by inflammatory bowel diseases, which comprises hyaluronic acid or a pharmaceutically acceptable salt thereof as an active ingredient (hereinafter referred to as "preventing or improving agent of the invention").

BRIEF DESCRIPTION OF THE DRAWINGS

The patent or application file contains at least one drawing executed in color. Copies of this patent or patent application publication with color drawings (s) will be provided by the Office upon request and payment of the necessary fee.

BEST MODE FOR CARRYING OUT THE INVENTION

Figure 1:
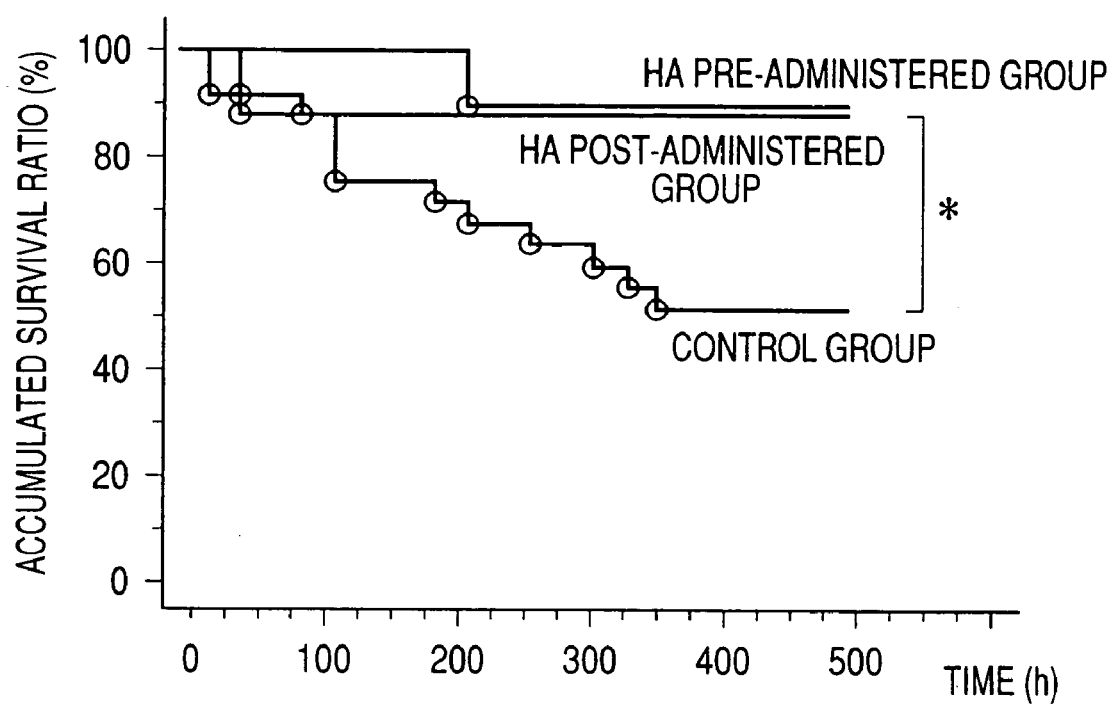
FIG. 1 is a graph showing improvement of survival rates (inhibition of survival period shortening) by administration of sodium hyaluronate (hereinafter referred to as "HA").

The present inventors have conducted intensive studies in order to solve the above problems and found, as a result, that hyaluronic acid shows markedly excellent effect on inflammatory bowel diseases, particularly symptoms accompanied by the inflammatory bowel diseases (diarrhea, weight loss, bowel tissues edema, cell infiltration, surviving period shortening, and the like), and its safety is also high. The present invention has been accomplished based on these findings.

The preventing or improving agent of the invention is preferably an agent for preventing or improving diarrhea, an agent for preventing or improving weight loss, an inhibitor for bowel tissue edema, an inhibitor for cell infiltration or an inhibitor for surviving period shortening.

Preferably, the treating agent of the invention and the preventing or improving agent of the invention can be intravenously administered. Also, the weight average molecular weight of the hyaluronic acid or the pharmaceutically acceptable salt thereof used as the active ingredient of the treating agent of the invention and the preventing or improving agent of the invention is preferably from 600,000 to 1,200,000, more preferably from 700,000 to 1,100,000, and more preferably from 800,000 to 1,000,000.

Furthermore, it is preferable that the inflammatory bowel disease which becomes the applying subject for the treating agent of the invention and the preventing or improving agent of the invention is Crohn disease or ulcerative colitis.

<1> Hyaluronic Acid or Pharmaceutically Acceptable Salt Thereof

The origin of the hyaluronic acid or a pharmaceutically acceptable salt thereof used in the present invention is not particularly limited, and any hyaluronic acid separated and purified from a cockscomb, an umbilical cord, a hyaluronic acid-producing microorganism and the like can be used. Particularly preferred are those which are purified to a high purity and do not substantially contain substances whose contamination is not acceptable as a medicament.

Examples of the useful pharmaceutically acceptable salt of hyaluronic acid include pharmaceutically acceptable salts among its salts with inorganic bases, such as alkali metal salts (sodium salt, lithium salt, potassium salt, and the like), alkaline earth metal salts, and ammonium salts; and salts with organic bases, such as diethanolamine salts, cyclohexylamine salts, and amino acid salts. Particularly preferred is HA.

Although the weight average molecular weight of the hyaluronic acid or the pharmaceutically acceptable salt thereof used in the present invention is not particularly limited, it is preferably from 600,000 to 1,200,000, more preferably from 700,000 to 1,100,000, far preferably from 800,000 to 1,000,000, most preferably from 850,000 to 950,000, and far most preferably about 900,000. Also, the weight average molecular weight of the hyaluronic acid or the pharmaceutically acceptable salt thereof used in the present invention can be calculated based on the formula of Laurent et al. (*Biochim. Biophys. Acta*, 42, 476 (1960)) by measuring its limiting viscosity in accordance with the General Test Methods, Article 36, Viscosity Measuring Method, The Pharmacopoeia of Japan, the 13th edition.

In addition, the limiting viscosity of the hyaluronic acid or the pharmaceutically acceptable salt thereof is from 11.5 to 20 dl/g at the weight average molecular weight of 600,000 to 1,200,000, from 13 to 18.5 dl/g at the weight average molecular weight of 700,000 to 1,100,000, from 14.5 to 17.5 dl/g at the weight average molecular weight of 800,000 to 1,000,000, from 15.0 to 16.5 dl/g at the weight average molecular weight of 850,000 to 950,000, and about 16 dl/g at the weight average molecular weight of about 900,000.

The treating agent of the invention and the preventing or improving agent of the invention having markedly excellent pharmacological activity can be prepared by using the above hyaluronic acid or the pharmaceutically acceptable salt thereof.

Also, the endotoxin concentration in the hyaluronic acid or the pharmaceutically acceptable salt thereof used in the present invention is preferably 0.3 EU/ml or less in the case of liquid preparations. Although the endotoxin concentration can be measured by using a generally used endotoxin measuring method well known to those skilled in the art, the Limulus test using a limulus amoebocyte lysate component is preferred. Additionally, the EU (endotoxin unit) can be measured and calculated in accordance with the Japan Industrial Standard, Biochemical Reagent Provisions (JIS K8008). Furthermore, the iron content is preferably 20 ppm or less.

<2> Dosage Form and the Like of the Treating Agent of the Invention etc.

The administration method of the treating agent of the invention and the preventing or improving agent of the invention is not particularly limited, so long as the effect of these preparations on inflammatory bowel diseases and symptoms accompanied thereby can be obtained, and examples include administration methods such as parenteral administration and oral administration. Among these, a parenteral administration is preferable, intravascular (intravenous or intraarterial) administration is more preferable, and intravenous administration is most preferable.

Hyaluronic acid or a pharmaceutically acceptable salt thereof can be appropriately formulated into the treating agent of the invention or the preventing or improving agent of the invention according to the administration method. Examples of the dosage form includes injections (solutions, suspensions, emulsions, solid preparations for dissolution before use, and the like), tablets, capsules, solutions, and the like. Among these, injections are preferable.

The concentration of the hyaluronic acid or the pharmaceutically acceptable salt thereof in the treating agent of the invention and the preventing or improving agent of the invention is not particularly limited, but it is preferably from 0.05 to 1% (w/v) when the dosage is a liquid form. Particularly, when the treating agent of the invention or the preventing or improving agent of the invention is provided as preparations for parenteral administration, for example as injections (solutions), the concentration is preferably from about 0.1 to 0.5% (w/v), more preferably from about 0.2 to 0.4% (w/v), and most preferably about 0.3% (w/v). Furthermore, when the treating agent of the invention or the preventing or improving agent of the invention is formulated into preparations for oral administration, for example into solutions, the concentration is preferably 0.1% (w/v) or more, and more preferably from about 0.2 to 1% (w/v).

When the treating agent of the invention or the preventing or improving agent of the invention is provided as injections, they may be in any of dissolved form, frozen form and freeze-dried form. The agents can be administered as injections by packing and sealing in appropriate containers, such as ampoules, vials, and syringes for injection, and by distributing or preserving as such.

The treating agent of the invention or the preventing or improving agent of the invention can be made into pharmaceutical preparations using conventionally known methods. In addition, other pharmaceutically active components and components generally used in medicaments, such as conventionally used stabilizers, emulsifying agents, osmotic pressure adjusting agents, buffer agents, tonicity agents, preservatives, soothing agents, coloring agents, fillers, binders, lubricants, and disintegrators, can be used in formulating the pharmaceutical preparations, so long as they do not have bad influence upon the hyaluronic acid or the pharmaceutically acceptable salt thereof and do not have influence upon the effects of the invention.

<3> Subject of Administration and the Like of the Treating Agent of the Invention etc.

The animals to which the treating agent of the invention and the preventing or improving agent of the invention are administered include human or non-human animals, and among these, vertebrae are preferable, mammals are more preferable, and human is most preferable.

The treating agent of the invention can be administered in order to treat inflammatory bowel diseases of these animals, such as prevention, inhibition of progress (prevention of worsening), improvement, treatment and the like of inflammatory bowel diseases. That is, the treating agent of the invention includes a preventing agent, a progress inhibiting (worsening preventing) agent, an improving agent, a treating agent and the like for inflammatory bowel diseases.

Furthermore, the preventing or improving agent of the invention can be administered in order to prevent or improve the above symptoms accompanied by inflammatory bowel diseases of animals. Examples of the "prevention or improvement of symptoms accompanied by inflammatory bowel diseases" include prevention or improvement of diarrhea, prevention or improvement of weight loss, inhibition of bowel tissue edema, inhibition of cell infiltration, inhibition of surviving period shortening, and the like, and as a result, a preventing or improving agent for diarrhea, a preventing or improving agent for weight loss, an inhibitor for bowel tissues edema, an inhibitor for cell infiltration, an inhibitor for surviving period shortening, and the like.

The treating agent of the invention and the preventing or improving agent of the invention can be broadly applied to inflammatory bowel diseases, and although not limited to specific diseases among the inflammatory bowel diseases, they can be suitably applied to Crohn disease and ulcerative colitis because they have particularly excellent effect upon a trinitrobenzenesulfonic acid (TNBS)-induced inflammatory bowel disease model which has been established and generally used as an inflammatory bowel disease model, as shown below in Examples.

Also, since the effect can be further improved by administering hyaluronic acid in advance (pre-administration) as shown below in Examples, the treating agent of the invention and the preventing or improving agent of the invention can be suitably used as a preventive agent.

The mixing amount, dose per once, administration interval, and the like of the hyaluronic acid or the pharmaceutically acceptable salt thereof in the treating agent of the invention and the preventing or improving agent of the invention should be individually decided according to the administration method, dosage forms, object for use, and the like of the treating agent of the invention, and the specific symptoms, age, sex, body weight, and the like of each patient, and are not particularly limited, so long as the effective amount thereof is administered, but the clinically effective amount of the hyaluronic acid or the pharmaceutically acceptable salt thereof is from 100 to 2,000 mg per once, or from 200 to 4,000 mg per day, per adult in the case of parenteral administration by injection, and is from 500 to 2,500 mg per once, or from 1,000 to 5,000 mg per day, per adult in the case of oral administration.

In addition, administration interval of the treating agent of the invention and the preventing or improving agent of the invention can be approximately once a day, or they can be administered by dividing the daily dose into 2 to 3 doses per day. They can also be administered approximately once in 1 to 3 days.

The present invention is specifically described below based on Examples. However, the technical scope of the present invention is not limited thereto.

<1> Materials and the Like

Firstly, tested substances and the like used in Examples are described.

(1) Tested Substances

Physiological saline

HA (weight average molecular weight: 900,000; limiting viscosity: 15.9 dl/g)

HA was used by dissolving in physiological saline to give a concentration of 0.3% (w/v). The endotoxin concentration after dissolution in physiological saline was 0.3 EU/ml or less in each case, and the iron content was 20 ppm in each case.

(2) Preparation of Inflammatory Bowel Disease Model

An inflammatory bowel disease model was prepared by carrying out irrigation of colon of a rat with 0.5 ml of 50 mg/ml TNBS (50% ethanol solution). The TNBS-induced inflammatory bowel disease model is a generally used model which has been established as an induced inflammatory bowel disease model (e.g., see GASTROENTEROLOGY, Vol. 109, No. 4, pp. 1344-1367 (1995), and the like).

<2> Effect of HA on Inflammatory Bowel Disease Model

In order to examine effect of HA on inflammatory bowel diseases, the following drug effect and pharmacological test was carried out using the inflammatory bowel disease model prepared in the above.

The inflammatory bowel disease model animals were divided into the following groups according to respective tested substances, and 2 ml of physiological saline solution (0.3% (w/v)) of each of the following tested substances was injected into the tail vein of each experimental animal.

| | |
|---|---|
| Physiological saline administered group (control group): | 25 animals |
| HA post-administered group: | 25 animals |
| HA pre-administered group: | 10 animals |

In the control group, the first administration was carried out just after the preparation of the above model, and then the administration was continuously carried out once a day for 20 days.

In the HA post-administered group, the first administration was carried out just after the preparation of the above model, and then the administration was continuously carried out once a day for 20 days.

In the HA pre-administered group, the first administration was carried out 24 hours before the preparation of the above model, and then the administration was continuously carried out once a day for 20 days.

During the administration period of tested substances, surviving conditions of the animals were observed every day. The results are shown in FIG. 1. Also, the symbol * in the drawing indicates that it is significant with a significant difference of $p=0.0086$ (Logrank test (Mantel-Cox test)).

As a result, the survival rate was significantly improved in each of the HA administered groups in comparison with the control group. Also, among the HA administered groups, the survival ratio was 100% after a lapse of 200 hours in the pre-administered group, showing that the survival rate was improved in comparison with the post-administered group. It was found based on these results that HA has the effect to inhibit surviving period shortening accompanied by inflammatory bowel diseases.

In addition, observation and measurement of the following points were carried out on the animals survived on the 20th day after the first administration.

(1) Conditions of Diarrhea

While diarrhea was severe in the control group, diarrhea was hardly observed in the HA administered groups. It was found based on this result that HA has the activity to prevent or improve the diarrhea accompanied by inflammatory bowel diseases.

(2) Body Weight

Results of the body weight measurement are shown below. Also, the following numerical values are expressed as "average value±standard error".

| | |
|---|---|
| Control group: | 175 ± 4 g |
| HA post-administered group | 203 ± 3 g |

As shown in the above, the weight loss was significantly inhibited in the HA administered group in comparison with the control group ($p<0.001$, Mann-Whitney U-test). It was found based on this result that HA has the activity to prevent or improve the weight loss accompanied by inflammatory bowel diseases.

(3) Bowel Tissue Edema

The large intestine was excised and cut open, and the contents were washed using physiological saline. After the adhered moisture was removed, the weight of the large intestine tissue was measured to calculate the weight per 1 cm bowel tissue. The results are shown below. Also, the following numerical values are expressed as "average value±standard error".

| | |
|---|---|
| Control group: | 448 ± 60 mg/cm bowel tissue |
| HA post-administered group | 51 ± 1 mg/cm bowel tissue |

As shown in the above, the bowel tissue edema was significantly inhibited in the HA administered group in comparison with the control group (p<0.001, Mann-Whitney U-test). It was found based on this result that HA has the activity to inhibit bowel tissue edema accompanied by inflammatory bowel diseases.

(4) Microscopic Observation of Bowel Tissue

Section samples of bowel tissue were prepared and observed under a light microscope.

Figure 2:
FIG. 2 is a photograph showing a light microscopic image (magnification: 640) of a bowel tissue section sample in the control group.
Figure 3:
FIG. 3 is a photograph showing a light microscopic image (magnification: 320) of a bowel tissue section sample in the HA post-administered group.

While edema and cell infiltration were significant in the control group (FIG. 2), edema was significantly alleviated and cell infiltration was also inhibited significantly in the HA post-administered group in comparison with the control group (FIG. 3). Based on this result, it was confirmed once more that HA has the activity to inhibit edema accompanied by inflammatory bowel diseases. In addition, it was found that HA has the activity to inhibit cell infiltration accompanied by inflammatory bowel diseases.

Also, as is apparent from the above results, HA is a material having high safety, because it is already used as the active ingredient of commercially available joint function improving agents and ophthalmic surgery assisting agents.

INDUSTRIAL APPLICABILITY

As is apparent from the results of the above drug effect and pharmacological tests, the treating agent of the invention and the preventing or improving agent of the invention containing hyaluronic acid or the pharmaceutically acceptable salt thereof as the active ingredient exert markedly excellent effect on inflammatory bowel diseases and symptoms accompanied thereby and have markedly high safety, so that they are markedly useful in treatment for inflammatory bowel diseases and the like. In addition, since it was shown that the treating agent of the invention and the preventing or improving agent of the invention have further superior effect by administering them in advance (pre-administration) to the subject of administration, they are particularly useful as preventive agents.

The invention claimed is:

1. A method for treating inflammatory bowel diseases, consisting essentially of administering parenterally or orally an effective amount of hyaluronic acid or a pharmaceutically acceptable salt thereof as an active ingredient to a human or a non-human animal in need of treatment and having at least one symptom accompanied by inflammatory bowel disease, wherein the effective amount is from 100 to 2,000 mg per dose parenterally or from 500 to 2,500 mg per dose orally.

2. A method for preventing or improving symptoms accompanied by inflammatory bowel diseases, consisting essentially of administering parenterally or orally an effective amount of hyaluronic acid or a pharmaceutically acceptable salt thereof as an active ingredient to a human or a non-human animal to prevent or improve at least one symptom accompanied by inflammatory bowel disease, wherein the effective amount is from 100 to 2,000 mg per dose parenterally or from 500 to 2,500 mg per dose orally.

3. The method according to claim 2, wherein the symptom is diarrhea.

4. The method according to claim 2, wherein the symptom is weight loss.

5. The method according to claim 2, wherein the symptom is bowel tissue edema.

6. The method according to claim 2, wherein the symptom is cell infiltration.

7. The method according to claim 2, wherein the symptom is survival period shortening.

8. The method according to claim 1, wherein the hyaluronic acid or the pharmaceutically acceptable salt thereof is intravenously administered.

9. The method according to claim 1, wherein the hyaluronic acid or the pharmaceutically acceptable salt thereof has a weight average molecular weight of 600,000 to 1,200,000.

10. The method according to claim 1, wherein the hyaluronic acid or the pharmaceutically acceptable salt thereof has a weight average molecular weight of 700,000 to 1,100,000.

11. The method according to claim 1, wherein the hyaluronic acid or the pharmaceutically acceptable salt thereof has a weight average molecular weight of 800,000 to 1,000,000.

12. The method according to claim 1, wherein the inflammatory bowel disease is Crohn disease or ulcerative colitis.

13. The method according to claim 2, wherein the hyaluronic acid or the pharmaceutically acceptable salt thereof is intravenously administered.

14. The method according to claim 2, wherein the hyaluronic acid or the pharmaceutically acceptable salt thereof has a weight average molecular weight of 600,000 to 1,200,000.

15. The method according to claim 2, wherein the hyaluronic acid or the pharmaceutically acceptable salt thereof has a weight average molecular weight of 700,000 to 1,100,000.

16. The method according to claim 2, wherein the hyaluronic acid or the pharmaceutically acceptable salt thereof has a weight average molecular weight of 800,000 to 1,000,000.

17. The method according to claim 2, wherein the inflammatory bowel disease is Crohn disease or ulcerative colitis.

* * * * *